United States Patent
Wang et al.

(10) Patent No.: US 9,664,632 B2
(45) Date of Patent: May 30, 2017

(54) CELL-IMPEDANCE SENSORS

(71) Applicant: CapitalBio Corporation, Beijing (CN)

(72) Inventors: Lei Wang, Beijing (CN); Keith Mitchelson, Beijing (CN); He Wang, Beijing (CN); Jing Cheng, Beijing (CN)

(73) Assignee: CapitalBio Corporation, Beijing (CN)

( * ) Notice: Subject to any disclaimer, the term of this patent is extended or adjusted under 35 U.S.C. 154(b) by 0 days.

(21) Appl. No.: 14/171,757

(22) Filed: Feb. 3, 2014

(65) Prior Publication Data

US 2014/0285215 A1 Sep. 25, 2014

Related U.S. Application Data

(62) Division of application No. 12/532,992, filed as application No. PCT/CN2007/002260 on Jul. 25, 2007, now Pat. No. 8,642,287.

(30) Foreign Application Priority Data

Apr. 25, 2007 (CN) .......................... 2007 1 0098717

(51) Int. Cl.
*G01R 27/28* (2006.01)
*G01N 27/06* (2006.01)
*G01N 33/487* (2006.01)
*G01N 33/543* (2006.01)
*G01N 27/22* (2006.01)

(52) U.S. Cl.
CPC .......... *G01N 27/06* (2013.01); *G01N 27/221* (2013.01); *G01N 33/48707* (2013.01); *G01N 33/48728* (2013.01); *G01N 33/5438* (2013.01)

(58) Field of Classification Search
CPC ...................... G01N 27/221; G01N 33/48707
USPC ....................................................... 324/649
See application file for complete search history.

(56) References Cited

U.S. PATENT DOCUMENTS

| | | | |
|---|---|---|---|
| 3,513,384 A | 5/1970 | Schneider | |
| 4,920,047 A | 4/1990 | Giaever et al. | |
| 5,187,096 A | 2/1993 | Giaever et al. | |
| 6,437,551 B1 | 8/2002 | Krulevitch et al. | |
| 6,758,961 B1 | 7/2004 | Vogel et al. | |
| 7,462,324 B2 | 12/2008 | Ozaki et al. | |
| 7,833,396 B2 | 11/2010 | Fukushima | |
| 2002/0182591 A1 | 12/2002 | Giaever et al. | |
| 2004/0128633 A1 | 7/2004 | Weller et al. | |
| 2004/0152067 A1* | 8/2004 | Wang et al. ...................... 435/4 |
| 2004/0163953 A1 | 8/2004 | Bhullar et al. | |
| 2005/0004442 A1 | 1/2005 | Ozaki et al. | |
| 2005/0067279 A1 | 3/2005 | Chen et al. | |
| 2005/0130119 A1 | 6/2005 | Giaever et al. | |
| 2005/0153425 A1 | 7/2005 | Xu et al. | |
| 2005/0213374 A1 | 9/2005 | Xu et al. | |
| 2005/0252777 A1 | 11/2005 | Li | |
| 2006/0105321 A1 | 5/2006 | Moy et al. | |
| 2006/0121446 A1 | 6/2006 | Abassi et al. | |
| 2006/0151324 A1 | 7/2006 | Davies et al. | |
| 2006/0188904 A1 | 8/2006 | Ozkan et al. | |
| 2007/0155015 A1 | 7/2007 | Vassanelli et al. | |
| 2007/0228403 A1 | 10/2007 | Choi et al. | |
| 2007/0296425 A1 | 12/2007 | LaMeres et al. | |
| 2008/0083617 A1 | 4/2008 | Simpson et al. | |
| 2008/0106884 A1 | 5/2008 | English et al. | |
| 2008/0286750 A1 | 11/2008 | Xu et al. | |
| 2009/0057147 A1 | 3/2009 | Kayyem | |
| 2009/0251155 A1 | 10/2009 | Wang et al. | |
| 2009/0322309 A1 | 12/2009 | Zhu et al. | |
| 2010/0184115 A1 | 7/2010 | Lei et al. | |

FOREIGN PATENT DOCUMENTS

| | | |
|---|---|---|
| CN | 1996001 | 7/2007 |
| TW | 200830963 | 7/2008 |
| WO | 2004010102 | 1/2004 |
| WO | 2004010103 | 1/2004 |

OTHER PUBLICATIONS

Solartron Analytical, 1260 Impedance/Gain-Phase Analyzer (2015) downloaded from www.solartronanalytical.com/download/To-view-the Model-1260A-Impedance-Gain-phase-Analyzer-pdf-click-here.pdf on Mar. 31, 2015.*
Olthuis et al. Theoretical and Experimental Determination of Cell Constants of Planar-Interdigitated Electrolyte Conductivity Sensors; Sensors and Actuators B, vol. 24-25 (1995) pp. 252-256.*
Saum et al. Use of Substrate Coated Electrodes and AC Impedance Spectroscopy for the Detection of Enzyme Activity; Biosensors and Bioelectronics, vol. 13 (1998) pp. 511-518.*
Arndt, S., et al., "Bioelectrical Impedance Assay to Monitor Changes in Cell Shape During Apoptosis," Biosensors and Bioelectronics, 19(6):583-594, Jan. 2004.
Bieberich, E., et al., "Neuronal Differentiation and Synapse Formation of PC12 and Embryonic Stem Cells on Interdigitated Microelectrode Arrays: Contact Structures for Neuron-to-Electrode Signal Transmission (NEST)," Biosensors and Bioelectronics, 19(8):923-931, Mar. 2004.
Bowen, C.R., et al., "Optimisation of interdigitated electrodes for piezoelectric actuators and active fibre composites," Journal of Electroceramics, 16:263-269, 2006.

(Continued)

*Primary Examiner* — Scott Long
*Assistant Examiner* — Paul Martin
(74) *Attorney, Agent, or Firm* — Perkins Coie LLP

(57) ABSTRACT

Systems, apparatus and methods for designing and operating a cell-electrode impedance sensor to detect chemical and biological samples, including biological cells. In one implementation, a method of designing a cell-electrode impedance sensor includes determining a cell free cell-electrode impedance and a cell covered cell-electrode impedance based on a design model for the cell-electrode impedance sensor, wherein the design model is based on one or more factors, the factors including properties and elements of a cell-electrode impedance measurement system, using the cell free cell-electrode impedance and the cell covered cell-electrode impedance to obtain a sensor sensitivity of the cell-electrode impedance measurement system, and choosing one or more design parameters of the cell-electrode impedance sensor in the cell-electrode impedance measurement system to maximize the sensor sensitivity.

17 Claims, 13 Drawing Sheets

(56) References Cited

OTHER PUBLICATIONS

European Search Report dated Apr. 21, 2010 for European Patent Application No. 08169204.8, filed Oct. 7, 2003 (9 pages).
Giaever, I., et al., "A morphological biosensor for mammalian cells," Nature, 366:591-592, Dec. 1993.
Giaever, I., et al., "Micromotion of Mammalian Cells Measured Electrically," Proceedings of the National Academy of Science of the USA, 88(17):7896-7900, Sep. 1991.
Giaever, I., et al., "Monitoring Fibroblast Behavior in Tissue Culture with an Applied Electric Field," Proceedings of the National Academy of Science of the USA, 81(12):3761-3764, Jun. 1984.
Greve, D.W., et al., "Modeling of impedance of cell-covered electrodes," Sensors Conference, Proceedings of IEEE, 2:1358-1363, 2003.
Huang, X., et al., "Simulation of microelectrode impedance changes due to cell growth," IEEE Sensors Journal, 4(5):576-583, 2004.
International Search Report dated Feb. 28, 2008 for International Application No. PCT/CN2007/002260, filed Jul. 25, 2007 (4 pages).
Jiang, X., et al., "Electrochemical desorption of self-assembled monolayers noninvasively releases patterned cells from geometrical confinements," Journal of the American Chemical Society, 125(9):2366-2367, Mar. 2003.
Nie, et al., "On-chip cell migration assay using microfluidic channels," Biomaterials, Elsevier science publishers, 28 (27):4017-4022, Jul. 2007.
Wang, L., et al., "An automatic and quantitative on-chip cell migration assay using self-assembled monolayers combined with real-time cellular impedance sensing," Lab on a Chip, 8(6):872-878, Jun. 2008.
Wegener, J., et al., "Electric Cell-Substrate Impedance Sensing (ECIS) as a Noninvasive Means to Monitor the Kinetics of Cell Spreading to Artificial Surfaces," Experimental Cell Research, 259(1):158-166, Aug. 2000.
Xiao, C., et al., "An in-depth analysis of electric cell-substrate impedance sensing to study the attachment and spreading of mammalian cells," Analytical Chemistry, 74(6):1333-1339, Feb. 2002.
Xiao, C., et al., "Online Monitoring of cell growth and cytotoxicity using electric cell-substrate impedance sensing (ECIS)," Biotechnology Progress, 19:1000-1005, 2003.
Xing, J.Z., et al., "Dynamic Monitoring of Cytotoxicity on Microelectronic Sensors," Chemical Research in Toxicology, 18(2):154-161, Feb. 2005.
Yong, Li, et al., "A method for patterning multiple types of cells by using electrochemical desorption of self-assembled monolayers within microfluidic channels," Angewandte Chemie, 46(7):1094-1096, 2007.
Yu, N., et al., "Real-time monitoring of morphological changes in living cells by electronic cell sensor arrays : An approach to study G protein-coupled receptors," Analytical Chemistry, 78(1):35-43, Jan. 2006.

\* cited by examiner

CELL-IMPEDANCE SENSORS

CROSS REFERENCE TO RELATED APPLICATIONS

This patent document is a divisional application of and claims priority to U.S. patent application Ser. No. 12/532,992, filed on Sep. 24, 2009, now U.S. Pat. No. 8,642,287, which is a U.S. National Stage under 35 U.S.C. §371 of International Patent Application No. PCT/CN2007/002260, filed on Jul. 25, 2007, which claims benefit of priority of Chinese Patent Application No. 200710098717.4, filed on Apr. 25, 2007. The entire contents of the before-mentioned patent applications are incorporated by reference as part of the disclosure of this application.

TECHNICAL FIELD

The present disclosure relates to detecting chemical and biological samples, including biological cells.

BACKGROUND

Living cells are surrounded by an outer cell membrane that restricts the movement of ions and solutes between the cell interior and the exterior of the cell. Changes in the electrical activity of cell membranes can reflect the biophysical state of the cells and further reflect underlying physiological and biochemical processes occurring within the cell, as well as biophysical changes occurring at the surface of the cell or in the cell membrane. Electrical devices and apparatus for the measurement of electrical impedance can be used to detect the state of the electrophysiological activity of living cells and their cell membranes.

Cell-electrode impedance sensing and cell substrate electrical impedance sensing are two related electrical measurements that are based on the application of a small alternating current (AC) electrical signal to probe the value of the impedance of sensor electrodes immersed in a conductive medium. Living cells can attach and grow on the surface of the sensor electrodes and can alter the electric field between electrodes causing a change in the electrical impedance that can be detected by the sensor electrodes. The measurement of impedance by the sensor can reflect the electrophysiological state of the cell and can allow the biophysical properties of the cell to be monitored.

SUMMARY

In one example, a method to design a cell-electrode impedance measurement system is described where a range of dimensions of a cell-electrode impedance sensor in the system can be determined based on a model for cell-electrode impedance to maximize sensor sensitivity. In addition, a frequency range to optimize the parameters of the sensor (e.g., sensitivity, dimensions, etc.) can also be determined.

In one aspect, a method of designing a cell-electrode impedance sensor is described. The method includes determining a cell free cell-electrode impedance and a cell covered cell-electrode impedance based on a design model for the cell-electrode impedance sensor, wherein the design model is based on one or more factors, the factors including properties and elements of a cell-electrode impedance measurement system, using the cell free cell-electrode impedance and the cell covered cell-electrode impedance to obtain a sensor sensitivity of the cell-electrode impedance measurement system, and choosing one or more design parameters of the cell-electrode impedance sensor in the cell-electrode impedance measurement system to maximize the sensor sensitivity.

This and other aspects can include one or more of the following features. The cell-electrode impedance sensor can include an interdigitated electrode array comprising a plurality of branch elements. The design parameters can include one or more of a width of the branch elements, a length of the branch elements, a surface area of the branch elements, and a number of the branch elements. The method can further include choosing an effective width lesser than the width chosen based on the design model, to account for a non-uniform electric field distribution over each branch element. The elements of the cell-electrode impedance measurement system can include one or more of a cell culture vessel, a cell culture substrate, and circuitry. The properties of the cell-electrode impedance measurement system can include one or more of a property of a cell culture medium and a property of the cell. Determining the cell free cell-electrode impedance and the cell covered cell-electrode impedance can include identifying values for the properties of the cell-electrode impedance measurement system, substituting the values in a first equation associated with the cell free cell-electrode impedance to determine the cell free cell-electrode impedance, and substituting the values in a second equation associated with the cell covered cell-electrode impedance to determine the cell covered cell-electrode impedance. The cell free cell-electrode impedance can be represented by a Helmholtz interfacial capacitance and a spreading resistance in the design model. The spreading resistance can be associated with a proportionality coefficient. The cell covered cell-electrode impedance can be represented by factors including one or more of a resistance between a plurality of cells, a capacitance between the plurality of cells, a resistance between a gap between a surface of a cell and a cell culture vessel substrate, and a capacitance between the surface of the cell and the cell culture vessel substrate. The resistance and capacitance between the plurality of cells, and the resistance and capacitance between the gap between the surface of the cell and the cell culture vessel substrate can each be associated with a proportionality coefficient. The resistance and capacitance between the plurality of cells, and the resistance and capacitance between the gap between the surface of the cell and the cell culture vessel substrate can depend on an extent of attachment between a surface of the cells and a surface of the sensor. The surface of the cells can be completely attached to the surface of the sensor. The surface of the cells can be partially attached to the surface of the sensor. Obtaining the sensor sensitivity of the system can further include determining the cell density of the system. The method can further include determining a frequency to deliver an alternating current (AC) signal to the sensor, wherein delivering the AC signal at the determined frequency can further improve sensor sensitivity. Determining the frequency can include determining a derivative of an equation for sensor sensitivity with respect to frequency and solving for the frequency by equating the derivative to zero.

In another aspect, an apparatus for measuring cell-electrode impedance in biological cells is described. The apparatus includes a cell-culture vessel that includes electrodes and circuitry electrically coupled to the electrodes. The electrodes are structured in an interdigitated array of electrode branch elements and the cell-culture vessel is operable to hold a cell-culture medium having biological cells attachable to the electrodes. The circuitry includes a stimulator to apply an alternating current (AC) signal to the electrodes and configured to control a frequency of the AC signal to be between 10 kHz and 40 kHz.

This and other aspects can include one or more of the following features. The electrodes can be located in the cell-culture vessel at a location to be immersed in the cell culture medium in the cell-culture vessel when the cell culture medium is present. The electrodes arranged in an interdigitated array of electrode branch elements include first electrode branch elements connected to a first electrical terminal of the circuitry and second electrode branch elements connected to a second electrical terminal of the circuitry, wherein the first and second electrode branch elements are interleaved and the circuitry applies the AC signal at the first and second electrical terminals. Each branch element can have a width. Adjacent branch elements can be separated by a distance. The branch element can have a width from 10 µm to 100 µm. A surface of the cells can be attached to a surface of each branch element. The cell-electrode impedance can depend on an extent of the attachment. A surface of the cells can be completely attached to the surface of the electrodes. A surface of the cells can be partially attached to the surface of the electrodes. A width of the branch elements can be altered to account for the extent of the attachment. The altered width can equal the sum of a width of the branch element and twice a radius of the biological cells.

In another aspect, a method for measuring cell-electrode impedance is described. The method can include immersing an interdigitated electrode array having electrode branch elements with a width from 10 µm to 100 µm in a cell culture medium in a cell-culture vessel to allow cells in the cell culture medium to attach to the electrode branch elements, and applying an alternating current (AC) signal to the interdigitated electrode array in a frequency range from 10 kHz to 40 kHz to measure a cell-electrode impedance for detecting cells.

This and other aspects can include one or more of the following features. The method can further include predetermining a number of branch elements, the branch element width, and a space between branch elements using a design model. The method can further include collecting an output from the electrode using a data acquisition module. The method can further include processing the collected output using a computer system. The method can further include providing input to the electrode using the computer system. The frequency range can be chosen to maximize a sensitivity of the electrode when employed in a cell-electrode impedance measurement system.

The system and techniques described can provide one or more advantages. Firstly, the cell-electrode impedance measurement system can be designed to maximize sensitivity of the system and to maximize the number of cells that can be studied. Further, a frequency of input AC signals can be determined which can further maximize sensitivity of the system. In addition, cell-electrode impedance sensors can be designed based on a design model.

The details of one or more implementations are set forth in the accompanying drawings and the description below. Other features and advantages will be apparent from the description and drawings, and from the claims.

DESCRIPTION OF DRAWINGS

Like reference symbols in the various drawings indicate like elements.

DETAILED DESCRIPTION

Figure 1:
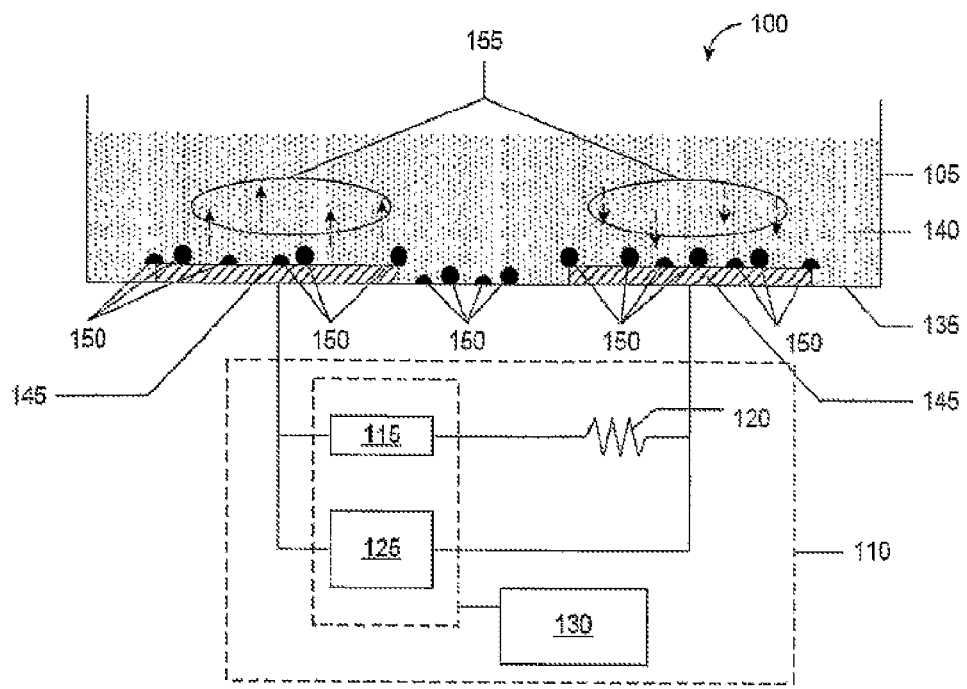
FIG. 1 is an example of a schematic of a cell-electrode impedance measurement system.

FIG. 1 depicts an example of a cell-electrode impedance measurement system 100. The system 100 can include a cell culture vessel 105 and circuitry 110. The cell culture vessel 105 can include elements to culture biological cells as well as elements to detect electrical properties of the biological cells, such as electrodes. The circuitry 110 can include elements to measure the electrical output produced by the physiological changes undergone by the cells in the cell culture vessel 105. The circuitry 110 can include an AC stimulator 115, a detection resistor 120, a data acquisition module 125, and a digital processor 130 (e.g., a computer). The AC stimulator can provide AC test signals at different frequencies for cell-electrode impedance sensing. The data acquisition module 125 can be used to collect output signals from the system 100. In some implementations, the output can include the voltage between two electrodes in the system 100. In other implementations, the output can include voltages between one or more pairs of electrodes in the system. In addition, the output can include current measurements, resistance measurements, etc. The rate of collection, for example, the number of voltage measurements per second, can be altered based on user input and the data acquisition module 125. The digital processor 130 can be used to store the data collected by the data acquisition module 125, process the data and perform additional operations related to the processed data. For example, the digital processor 130 may be configured to prepare spread sheets, perform statistical operations such as averaging, perform calculations such as calculating impedance from measured voltages, currents, and resistances, etc., as well as transferring the data by methods including storing on a portable storage device (e.g., compact disc, USB flash drive, etc.), transmitting over a network (e.g., wired, wireless, the internet), etc. The digital processor 130 can also be configured to provide input signals to the system 100 to alter experimental conditions, e.g., frequency of AC signals from the AC stimulator 115. In addition, the digital processor 130 can be configured to receive input from a user. Such input can include constants for use in data processing, input to alter experimental conditions, etc.

The system 100 can include a cell culture vessel 105. The cell culture vessel 105 can include a vessel substrate 135, a cell culture medium 140. Electrodes 145 can be positioned in the cell culture vessel 105. The electrodes 145 can be immersed in the cell culture medium 140. In some implementations, the electrodes 145 can be arranged as an interdigitated array and positioned such that a large surface area of the electrodes are available upon which the cells in the cell culture vessel can rest. The cell culture vessel 105 can contain the biological cells 105 under study. The cell culture vessel 105 can be manufactured from a bio-compatible insulating material, e.g., plastic, glass, polydimethylsiloxane (PDMS), etc. The vessel substrate 135 can be manufactured from the same material as the cell culture vessel 105. The cell culture medium 140 can include proteins, sugar, salt, amino acids, antibiotics, and other nutrition that cells need. Cells 150 growing in the cell culture vessel 105 can form a monolayer on the surface of the cell culture vessel 105 as well as the surface of the electrodes 145. Examples of cells that can be studied include HeLa, HepG2, NIN-3T3, VERO, etc. Properties of the cells that can be studied include cell proliferation, cell apoptosis, cell differentiation, cell migration, cell micromotion, cell attachment, etc. The cells 150 can be of several shapes (e.g., spherical, hemispherical, etc.). A cell 150 can be attached either completely or partially to the surface of the electrode 145. When a cell 150 is partially attached, only a portion of the cell 150 can be in contact with the surface of the electrode 145. In addition, a cell can be attached to the surface of the cell culture vessel 105 and can have no contact with the surface of the electrode 145.

In some implementations, the AC stimulator 115 can be designed and operated to supply an input AC voltage at a pre-determined frequency. The frequency can be altered based on user input. The cell culture medium 140 and the electrode 145 effectuate a part of a circuit through which a probe current 155 is flowed. The presence of cells on the electrode surface 145 can cause impedance which can affect the probe current 155. The probe current 155 can be affected by cells that are attached completely or partially attached to the surface of the electrodes 145. The voltage between two electrode surfaces 145 can be collected by the data acquisition module 125 and stored in the digital processor 130. Alternatively, or in addition, the probe current can be collected and stored in the digital processor 130. The digital processor 130 can be configured to calculate the impedance due to the cells 150 for every instance that the voltage and/or the probe current between the electrode surfaces 145 were recorded. In this manner, the cell-impedance of the system 100 can be determined.

Figure 2:
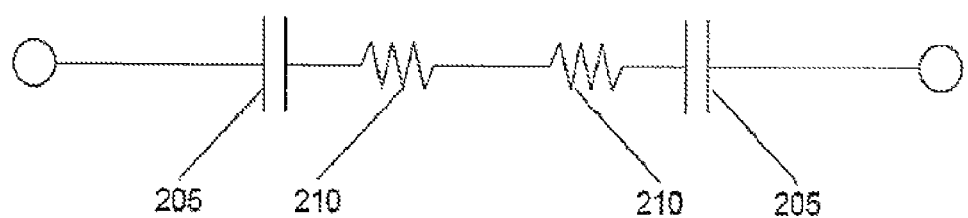
FIG. 2 is an example of an equivalent circuit for cell free cell-electrode impedance.

The impedance of the system described in FIG. 1 can be attributed to at least two sources, namely the cells 150 in the cell culture vessel 105 and the cell culture vessel 105 itself. In the absence of cells 150, the system 100 is a cell-free cell-electrode impedance sensor. FIG. 2 depicts an example of a schematic of an equivalent circuit for cell-free cell-electrode impedance for the system 100 in FIG. 1. The equivalent circuit depicts representations of the Helmholtz double layer interfacial capacitance, $C_I$ (205) and the spreading resistance of the cell culture media, $R_S$ (210).

Figure 3A:
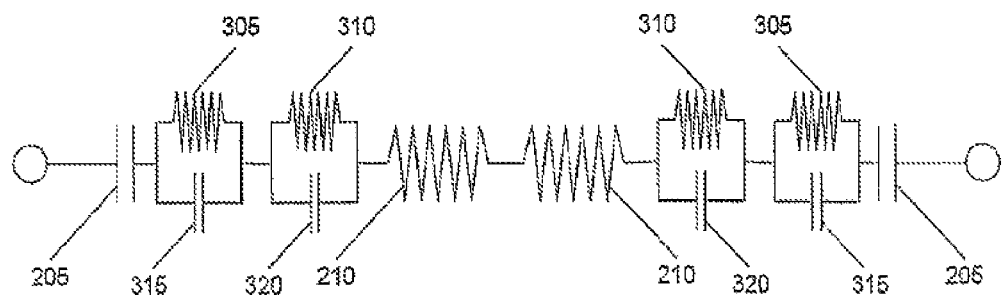
FIG. 3A is an example of an equivalent circuit for cell covered cell-electrode impedance.

FIG. 3A depicts an example of an equivalent circuit for cell covered cell-electrode impedance for system 100. When cells attach and grow on the electrode surface 145, the impedance of the cells 150 to the flow of probe current 155 can be modeled by the equivalent circuit shown in FIG. 3A. The impedance can be a function of the electrical resistance between growing cells, $R_{cell}$ (310). In addition, the cells which can be attached on the electrode surface 145 can be treated as a capacitance, $C_{cell}$ (320), which can be a biophysical property of the insulating cell membrane. A gap can be present between a cell 150 growing on the substrate surface and the underside of the attached cell 150. The gap between the underside of the cell 150 and the surface of the substrate can be composed of the cell culture medium 140 and can cause a resistance, $R_{gap}$ (305) and a capacitance, $C_{gap}$ (315). The values of $R_{cell}$ (310), $C_{cell}$ (320), $R_{gap}$ (305), and $C_{gap}$ (315) for a cell 150 can depend on factors including one or more of the extent of attachment of the cell 150 to the substrate surface, the biological nature of the cell, the cell culture medium 140, etc.

In some implementations, in measuring cell-electrode impedance, the sensitivity of the system 100 can be defined as the smallest impedance, caused by presence of cells in the cell culture vessel 105, that can be measured. The total impedance measured by the system 100 can be a function of the impedance due to the cells 150, the impedance due to the cell culture medium 140, and the density of cells, $Q_{cell}$. In some implementations, the sensitivity of the system 100 can be a function of the cell free cell-electrode impedance ($Z_{cell\ free-total}$), the cell covered cell-electrode impedance ($Z_{cell-covered-total}$), and the cell density, $Q_{cell}$, and can be depicted by equation (1).

$$\text{Sensitivity}(f) = \frac{|Z_{cell-covered-total}(f)| - |Z_{cell-free-total}(f)|}{Q_{cell}} \quad (1)$$

The impedance of the system 100 can be affected by the frequency, f, of the signal from the AC stimulator 115.

Figure 3B:
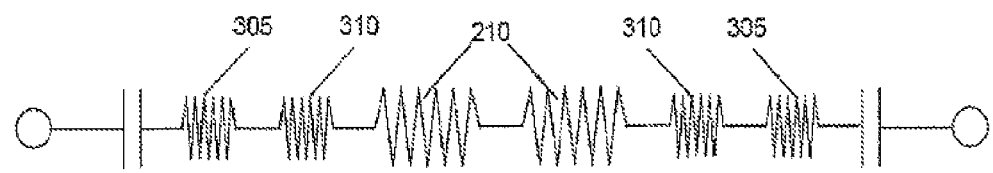
FIG. 3B is an example of an equivalent circuit for cell covered cell-electrode impedance when in low frequency range.

FIG. 3B depicts an equivalent circuit model for cell impedance when the applied AC signal to the electrodes of the sensor is in a selected low frequency range. For example, this selected low frequency can range between $[(1/10) \times (\pi \cdot R_{cell} \cdot C_{cell})]$ and $[(1/10) \times (\pi \cdot R_{gap} \cdot C_{gap})]$. In the low frequency range, the resistance of the cells, $R_{cell}$ (310), and the resistance of the gaps, $R_{gap}$ (305), dominate over the capacitance of the cells, $C_{cell}$ (320), and the capacitance of the gaps, $C_{gap}$ (315).

Figure 3C:
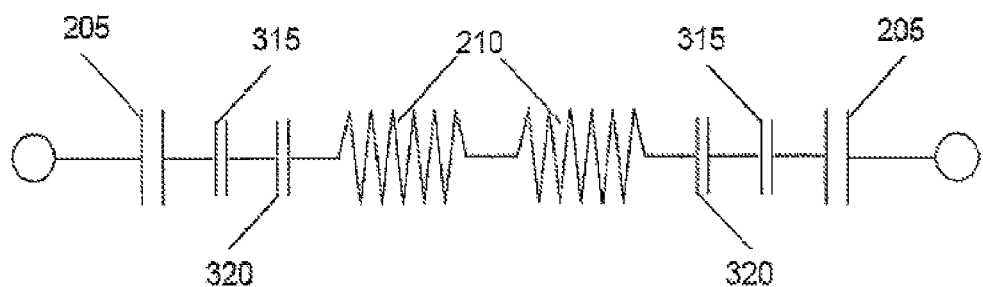
FIG. 3C is an example of an equivalent circuit for cell covered cell-electrode impedance when in high frequency range.

FIG. 3C depicts an equivalent circuit model for cell impedance when the applied AC signal to the electrodes of the sensor is in a selected high frequency range. For example, this high frequency can range between $[(5/2) \times (\pi \cdot R_{cell} \cdot C_{cell})]$ and $[(5/2) \times (\pi \cdot R_{gap} \cdot C_{gap})]$. In the high frequency range, the capacitance of the cells, $C_{cell}$ (320), and the capacitance of the gaps, $C_{gap}$ (315), dominate over the resistance of the cells, $R_{cell}$ (310), and the resistance of the gaps, $R_{gap}$ (305). The impedance of the system 100 can also be affected by the geometry of the cell-electrode impedance sensor.

Figure 4:
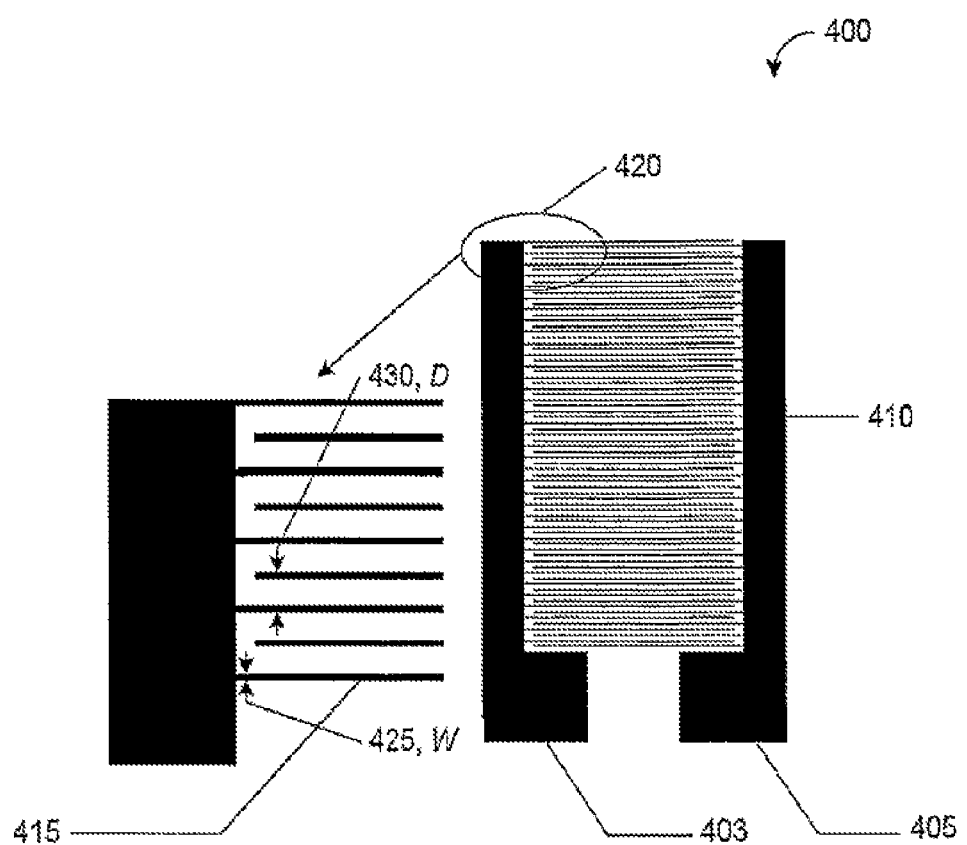
FIG. 4 is an example of a cell-electrode impedance sensor.

FIG. 4 depicts an example of a schematic of a cell-electrode impedance sensor 400. The sensor 400 can include two electrodes 403 and 405. The two electrodes 403 and 405 can be configured to form an interdigitated array 410 formed of interleaved branch elements 415 where each branch element 415 is connected to one sensor electrode 403 or 405 and the interleaved branch elements 415 include one group of branch elements 415 connected to the sensor electrode 403 and another group of branch elements 415 connected to the other sensor electrode 405. Referring to both FIGS. 1 and 4, the first group of branch elements is connected to a first electrical terminal of the circuitry 110 and the second group of branch elements is connected to a second electrical terminal of the circuitry 110. The branch elements of the first and the second group can be interleaved and the circuitry 110 applies the AC signal at the first and second electrical terminals. In some implementations, the branch elements 415 of each electrode can be arranged in an alternating manner. Alternatively, the branch elements 415 can be arranged in any order, for example, sequentially, alternatively, staggered, etc. In some implementations, the branch elements 415 can also be positioned on both sides of each electrode.

FIG. 4 also depicts a magnified view 420 of a portion of the sensor 400. The magnified view 420 illustrates branch elements 415 of the sensor. In the example illustrated in FIG. 4, the branch elements 415 of each electrode 405 are arranged in an alternating manner. In some implementations, the branch elements 415 can have a width, W (425). Two adjacent branch elements 15 can be separated by a distance, D (430). In some implementations, the branch elements 415 of both electrodes 405 can have a uniform width, W (425). In other implementations, the width, W (425), of the branch elements 415 of the same electrode 405 can be uniform. The width, W (425), of branch elements 415 of different electrodes can be non-uniform. In other implementations, the width, W (425), of each branch element 415 in the same electrode 405 can be non-uniform. In some implementations, the distance, D (430), between two branch elements 415 can be uniform. In other implementations, the branch elements 415 can be staggered with a non-uniform distance, D (430), separating the branch elements 415.

The sensitivity of a sensor can depend on factors including the design parameters of the sensor 400. The design parameters of the sensor 400 can include the material used to fabricate the sensor 400, the width, W (425), of each branch element 415, the distance between two branch elements, D (430), the length of the branch element 415, etc. The total area of the electrode can be represented by $A_{total}$. The total length of the sensor 400 can be represented by $L_{total}$. In some implementations, the length of each branch element 415 can be uniform. In such implementations, the total length of the electrode, $L_{total}$, can be represented by the length of each branch element, L, and the number of branch elements, N. In some implementations, the branch element 415 can have a width between 10 μm and 100 μm, or between 10 μm and 80 μm, such as one of 20 μm, 40 μm, and 60 μm for a range of sensing applications. The distance between two branch elements can be 20 μm in some sensor designs. The sensor 400 can be fabricated using various materials such as glass, silicon, certain plastics, etc. by methods including standard lift-off fabrication method. One method to determine optimal design parameters of a sensor is to fabricate sensors of different design parameters and employ each sensor in a cell-electrode impedance measurement system.

In some implementations, a design model based on fundamental principles can be developed to predict the cell free cell-electrode impedance and cell covered cell-electrode impedance of a cell-electrode impedance system 100. Based on the predicted impedance and given the conditions of the cell impedance measurement system 100, the design parameters of the sensor, such as branch element 415 dimensions, can be determined to optimize the system 100 to increase sensitivity and increase number of cells detected. In addition, the design model can be employed to determine an optimal frequency to maximize sensitivity of the system 100.

The total impedance measured by the system 100 can be a function of the impedance due to the cells and the impedance due to the electrode. The impedance due to the electrode, represented by $Z_{cell\text{-}free\text{-}total}$, can be determined using equation (2).

$$Z_{cell\text{-}free\text{-}total}(f) = \frac{2R_S + 2(j2\pi f C_I)^{-1}}{N} \qquad (2)$$

$$= \frac{2R_S + 2(j2\pi f C_I)^{-1}}{L_{total}/2L}$$

When cells attach and grow on the surface of the sensor 400, the impedance due to the cells, represented by $Z_{cell\text{-}covered\text{-}total}$, can be determined using equation (3).

$$Z_{cell\text{-}covered\text{-}total}(f) = \frac{2R_S + 2(j2\pi f C_I)^{-1} + 2\left(\frac{R_{cell} \times (j2\pi f C_{cell})^{-1}}{R_{cell} + (j2\pi f C_{cell})^{-1}} + \frac{R_{gap} \times (j2\pi f C_{gap})^{-1}}{R_{gapl} + (j2\pi f C_{gap})^{-1}}\right)}{N} \qquad (3)$$

$$= \frac{2R_S + 2(j2\pi f C_I)^{-1} + 2\left(\frac{R_{cell} \times (j2\pi f C_{cell})^{-1}}{R_{cell} + (j2\pi f C_{cell})^{-1}} + \frac{R_{gap} \times (j2\pi f C_{gap})^{-1}}{R_{gapl} + (j2\pi f C_{gap})^{-1}}\right)}{L_{total}/2L}$$

In the equivalent circuit equations (1) and (2), the interfacial capacitance, $C_I$ (205) can be a function of the permittivity of free space, $\varepsilon_0$, the effective dielectric constant of the double layer separating the ionic charges and the electrode, $\varepsilon_\rho$, area of a single electrode branch element 415, A, and the thickness of the double layer, $d_{dl}$. The interfacial capacitance, $C_I$ (205) can be determined using equation (4).

$$C_I = \frac{\varepsilon_0 \varepsilon_\rho A}{d_{dl}} \qquad (4)$$

In the equivalent circuit equations (1) and (2), the spreading resistance, $R_S$ (210) can be a function of the resistivity of the cell culture medium 140, ρ, the area of a single electrode branch element 415, A, and a proportionality coefficient, K. The spreading resistance, $R_S$ (210) can be determined using equation (5) below:

$$R_S = \frac{\rho K}{\pi A} \qquad (5)$$

In the equivalent circuit equation (2), the resistance of the gaps between cells, $R_{cell}$ 310, and the resistance of the cells to the gap between the cell and the substrate, $R_{gap}$ 305, can be inversely proportional to the electrode area, A. The capacitance of the cells that are attached to the electrode surfaces, $C_{cell}$ 320, and the capacitance of the gap between the cell and the substrate, $C_{gap}$ 315, can be directly proportional to the electrode area, A. The resistances and the capacitances can be represented by equation (6) below:

$$R_{cell}=K_1A^{-1}; R_{gap}=K_2A^{-1}; C_{cell}=K_3A; C_{gap}=K_4A \qquad (6)$$

The proportionality coefficients, K, $K_1$, $K_2$, $K_3$, and $K_4$ can be determined empirically. In one example, experimental data can be fitted to the design model using the least square fitting or other fitting algorithm. In some implementations, the values of the proportionality coefficients can be 85 ohm·mm² and 48 ohm·mm² for $K_1$ and $K_2$, respectively, and 60 nF/mm² and 6 nF/mm² for $K_3$ and $K_4$, respectively.

Substituting equation (6) in equation (2) and equation (3), the impedance due to the electrode, $Z_{cell-free-total}$, and the impedance due to the cells, $Z_{cell-covered-total}$, can be represented by equation (7) and equation (8), respectively:

$$Z_{cell-free-total}(f) = \frac{2\left(\frac{\rho K}{\pi} + \left(j\pi f \frac{\varepsilon_0 \varepsilon_\rho}{d_{dl}}\right)^{-1}\right)}{A.N} \qquad (7)$$

$$= \frac{2\left(\frac{\rho K}{\pi} + \left(j\pi f \frac{\varepsilon_0 \varepsilon_\rho}{d_{dl}}\right)^{-1}\right)}{A.L_{total}/2L}$$

$$Z_{cell-covered-total}(f) = \frac{2\left(\frac{\rho K}{\pi} + \left(j\pi f \frac{\varepsilon_0 \varepsilon_\rho}{d_{dl}}\right)^{-1}\right) + 2\left(\frac{K_1 \times (j2\pi f K_3)^{-1}}{K_1 \times (j2\pi f K_3)^{-1}} + \frac{K_2 \times (j2\pi f K_4)^{-1}}{K_2 + (j2\pi f K_4)^{-1}}\right)}{A.N} \qquad (8)$$

$$= \frac{2\left(\frac{\rho K}{\pi} + \left(j\pi f \frac{\varepsilon_0 \varepsilon_\rho}{d_{dl}}\right)^{-1}\right) + 2\left(\frac{K_1 \times (j2\pi f K_3)^{-1}}{K_1 \times (j2\pi f K_3)^{-1}} + \frac{K_2 \times (j2\pi f K_4)^{-1}}{K_2 + (j2\pi f K_4)^{-1}}\right)}{A.L_{total}/2L}$$

According to equations (7) and (8), the cell free cell-electrode impedance and the cell covered cell-electrode impedance are inversely proportional to the electrode area, A, and the total length of the electrode, $L_{total}$. The total length of the electrode, $L_{total}$, can be expressed as a function of the length of each branch element 415, L, and the number of branch elements, N. The total length of the electrode, $L_{total}$, can be expressed by equation (9).

$$L_{total}=2LN \qquad (9)$$

Equations (7) and (8) show that the cell free cell-impedance ($Z_{cell-free-total}(f)$) and the cell covered cell-impedance ($Z_{cell-covered-total}(f)$) are inversely proportional to the length of each branch element 415, L, and the number of branch elements, N. From equation (1), it can be determined that the sensitivity of the cell-impedance sensor is inversely proportional to the length of each branch element 415 and the number of branch elements. Therefore, in the design of a cell-electrode impedance sensor, the reduction of electrode branch number or a reduction in the electrode width can improve the sensitivity of the sensor, but can decrease the number of cells which could be monitored by the sensor.

Figure 5A:
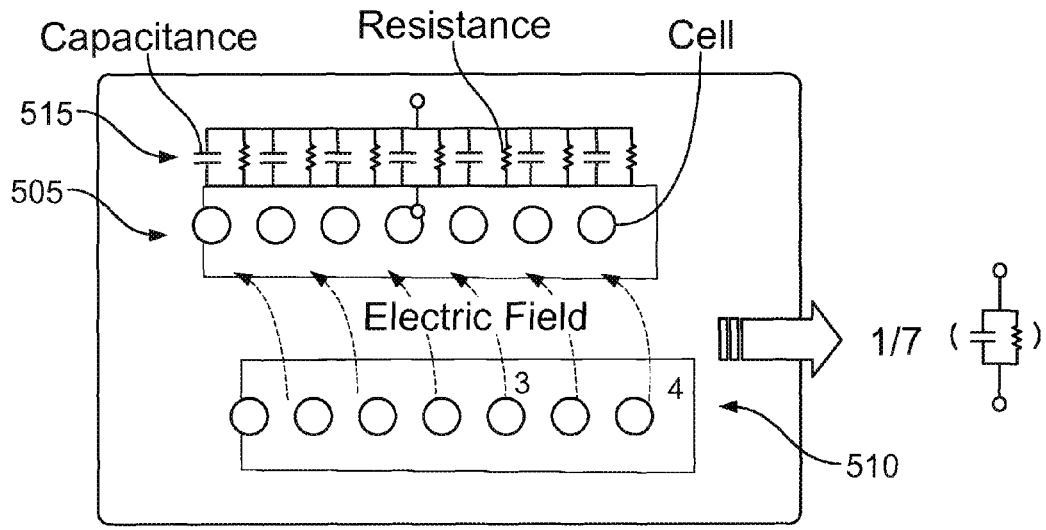
FIG. 5A is an example of cell-electrode impedance sensor and an equivalent circuit for cell-electrode impedance.
Figure 5B:
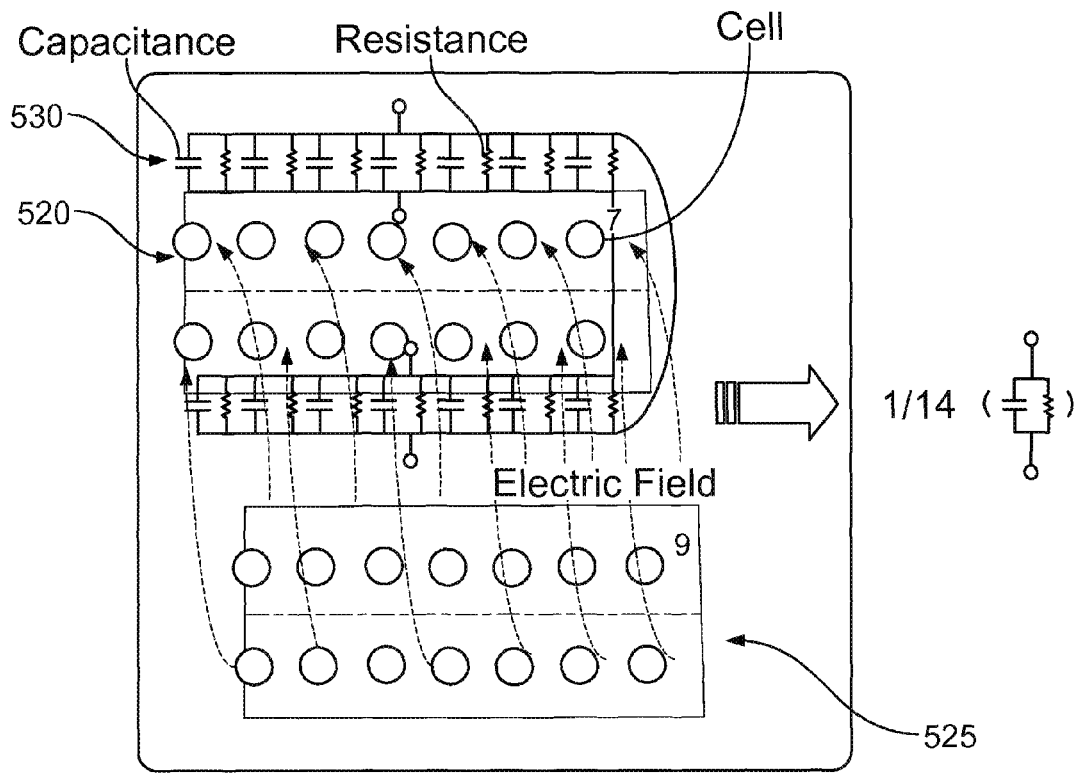
FIG. 5B is an example of cell-electrode impedance sensor and an equivalent circuit for cell-electrode impedance.

FIG. 5A and FIG. 5B show examples of cell-electrode impedance sensors including branch elements of different areas. The cell-electrode impedance sensor depicted in FIG. 5A includes two branch elements 505 and 510. The cell-electrode impedance sensor depicted in FIG. 5B includes two branch elements 520 and 525. In the examples shown, the areas of 505 and 510 are equal to each other while the areas of 520 and 525 are equal to each other. The area of the branch elements 505 and 510 is twice the area of the branch elements 520 and 525 in FIG. 5B. The equivalent circuit of cell-electrode impedance in FIG. 5A and FIG. 5B are represented by 515 and 530, respectively. In FIGS. 5A and 5B, the resistance represents the sum of $R_{cell}$ (310) and $R_{gap}$ (305) and the capacitance represents the sum of $C_{cell}$ (320) and $C_{gap}$ (315). In the example shown, each branch element 505 and 510 contain 7 cells attached to their surface. The equivalent circuit of each cell represents $R_{cell}$ (310), $R_{gap}$ (305), $C_{cell}$ (320), and $C_{gap}$ (315). Therefore, the total resistance and capacitance of cell culture vessel 505 is associated a factor of 1/7. In the example shown, the surface of each electrode of cell culture vessel 510 contains twice the number of cells attached as the surface of electrodes of cell culture vessel 515. The equivalent circuit of each cell represents $R_{cell}$ (310), $R_{gap}$ (305), $C_{cell}$ (320), and $C_{gap}$ (315). Therefore, the total resistance and capacitance of cell culture vessel 510 is associated a factor of 1/14. An electric field is generated between the electrodes 505 and 510 and the electrodes 520 and 525 when a voltage is applied.

Figure 6:
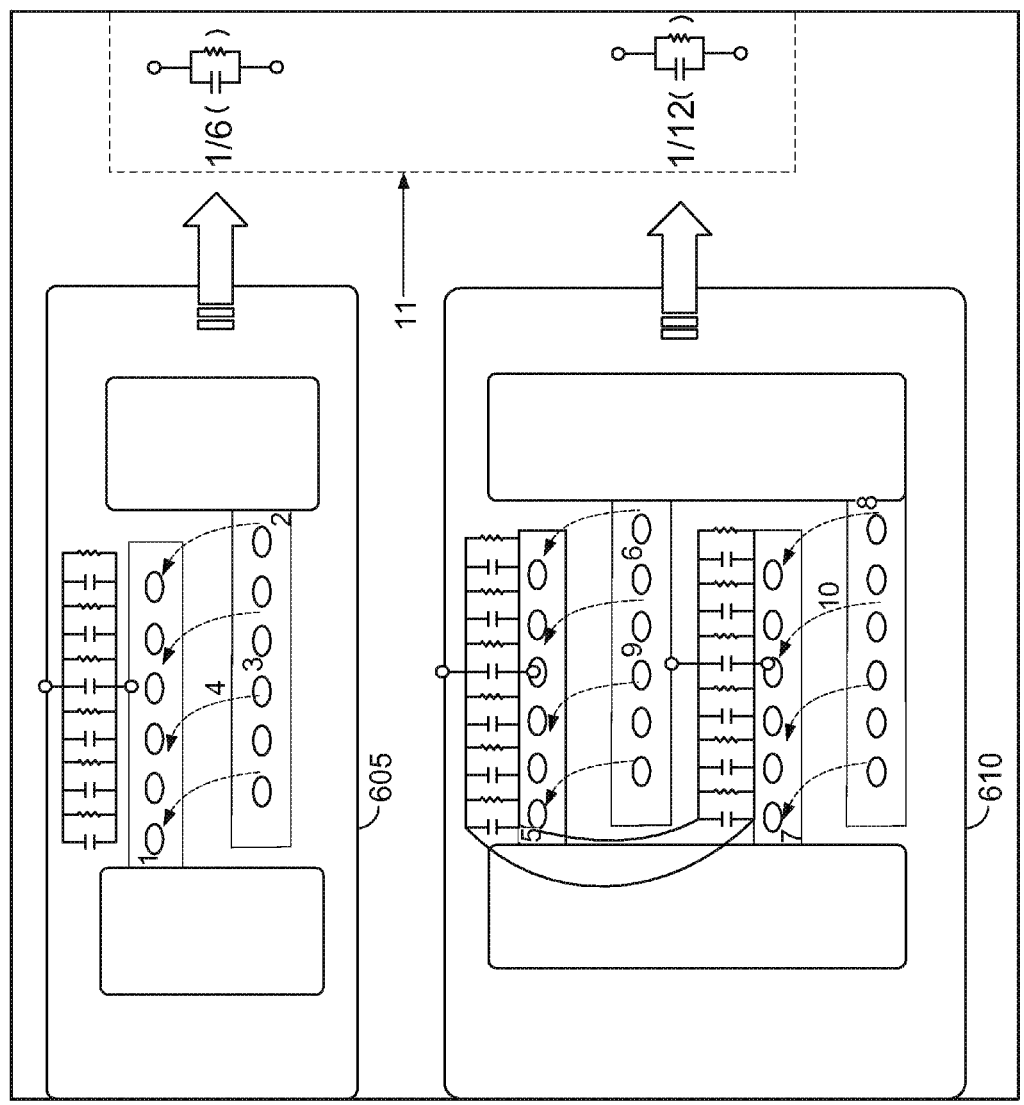
FIG. 6 is an example of equivalent circuits of sensor electrodes with different lengths.

FIG. 6 depicts an example of equivalent circuits of a cell-electrode impedance measurement systems of different lengths. The number of branch elements 415 in cell culture vessel 610 is twice the number of branch elements 415 in cell culture vessel 605. Thus, in the example shown, the total length of the electrodes in cell culture vessel 610 is twice that of the electrodes in the cell culture vessel 605. The equivalent circuit of each cell represents $R_{cell}$ (310), $R_{gap}$ (305), $C_{cell}$ (320), and $C_{gap}$ (315). In the example shown, the surface of each electrode in both culture vessels contains the same number of cells attached. Since the number of branch elements 415 in cell culture vessel 610 is twice the number of branch elements 415 in cell culture vessel 605, the number of cells attached to the branch elements 415 of cell culture vessel 610 is twice the number of cells attached to the branch elements 415 of cell culture vessel 605. Therefore, the total resistance and capacitance of cell culture vessel 605 are associated with a factor of 1/6. The total resistance and capacitance of cell culture vessel 610 are associated with a factor of 1/12.

Figure 7:
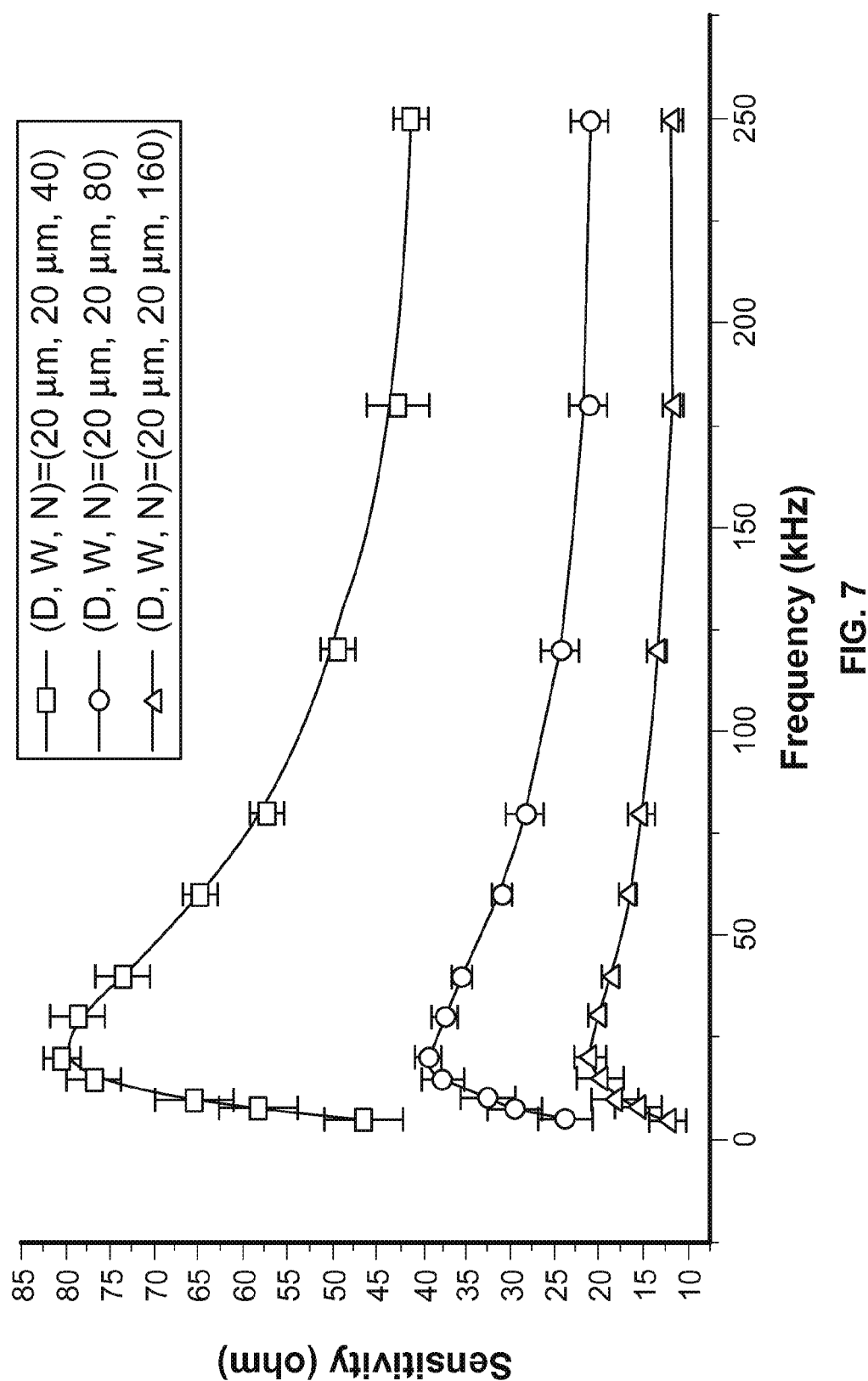
FIG. 7 is a plot of sensor sensitivity in response to changing frequency.

FIG. 7 depicts a plot of sensor sensitivity in response to frequency for three different values for the total electrode length, $L_{total}$. The total electrode length, $L_{total}$, is altered by increasing the number of branch elements 415, N. The number of branch elements in the sensors tested were 40, 80, and 160. The width of the branch element, W, and the inter-electrode spacing, D, were maintained constant at 20 µm and 20 µm, respectively. As depicted in FIG. 7, the sensitivity (in ohms) increased at the frequency range of 0-40 kHz and decreased for frequencies greater than 40 kHz.

Figure 8:
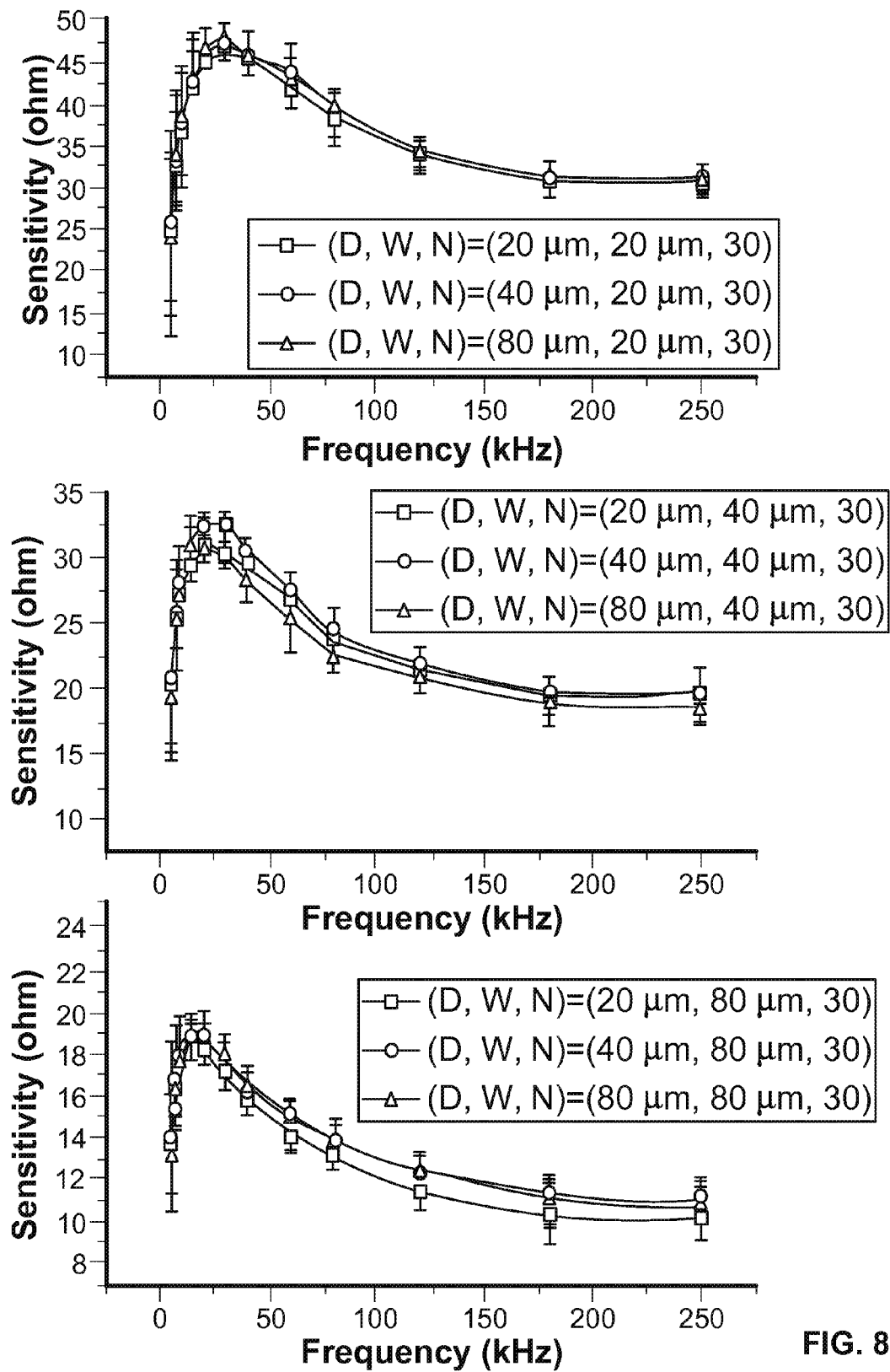
FIG. 8 is a plot of sensor sensitivity in response to changing frequency.

FIG. 8 depicts a plot of sensor sensitivity in response to frequency for different values for the inter-electrode distance, D. In one example, the number of branch elements 415 was 60 and the width of the electrode, W, was 20 µm. The inter-electrode spacing, D, was 20 µm, 40 µm, and 80 µm. In a second example, the number of branch elements 415 was 60 and the width of the electrode, W, was 40 µm. The inter-electrode spacing, D, was 20 µm, 40 µm, and 80 µm. In a third example, the number of branch elements 415 was 60 and the width of the electrode, W, was 80 µm. The inter-electrode spacing, D, was 20 µm, 40 µm, and 80 µm. As depicted in FIG. 8, the sensitivity (in ohms) was not affected by the change in inter-electrode spacing, D.

Figure 9:
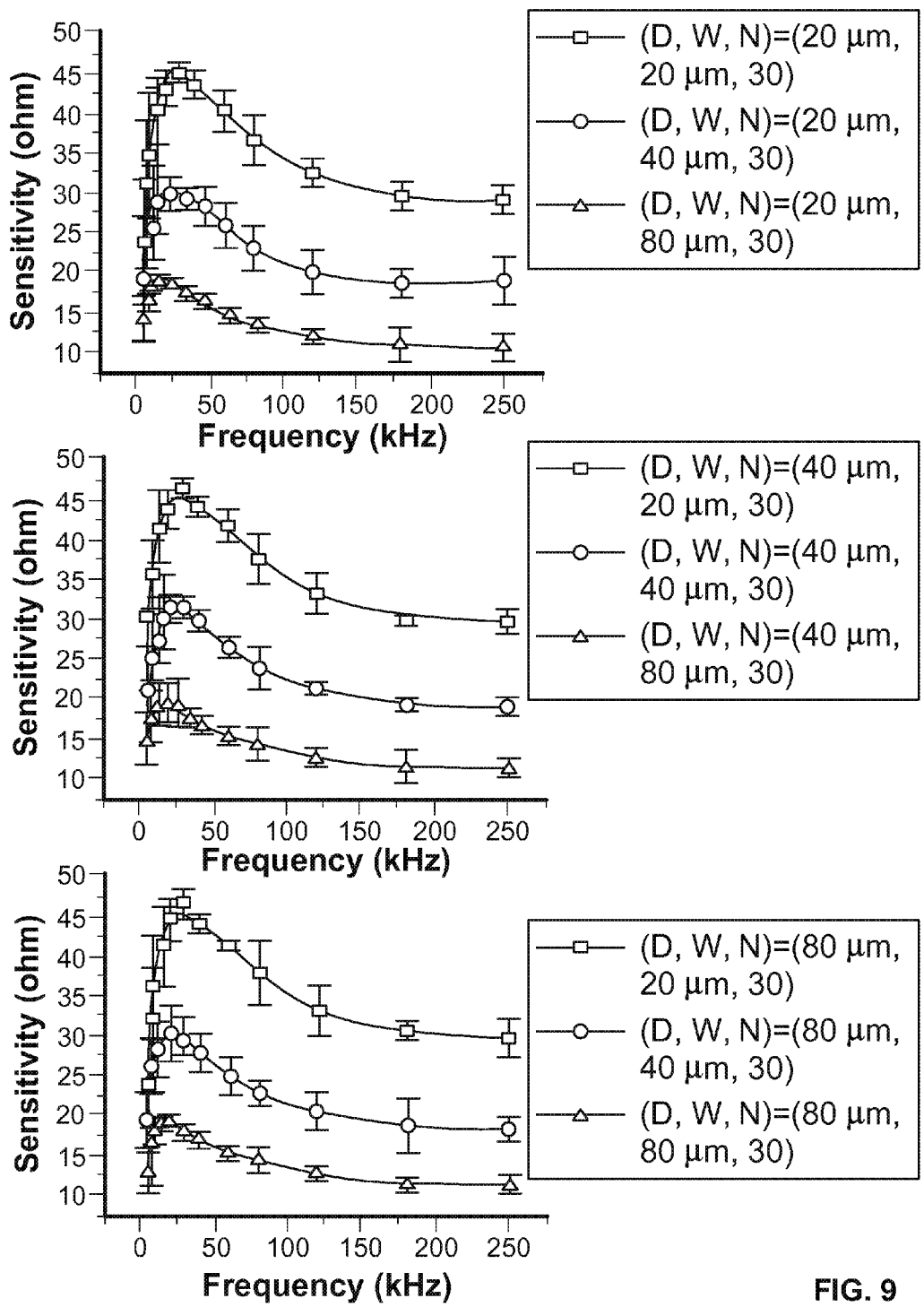
FIG. 9 is a plot of sensor sensitivity in response to changing frequency.

FIG. 9 depicts a plot of sensor sensitivity in response to frequency for different values of the electrode width, W. In one example, the number of branch elements 415 was 60 and the inter-electrode distance, D, was 20 µm. The width, W, was 20 µm, 40 µm, and 80 µm. In a second example, the number of branch elements was 60 and the inter-electrode distance, D, was 40 µm. The width, W, was 20 µm, 40 µm, and 80 µm. In a third example, the number of branch elements 415 was 60 and the inter-electrode distance, D, was 80 µm. The width, W, was 20 µm, 40 µm, and 80 µm. As depicted in FIG. 7, the sensitivity (in ohms) decreased with increasing width, W.

Figure 10:
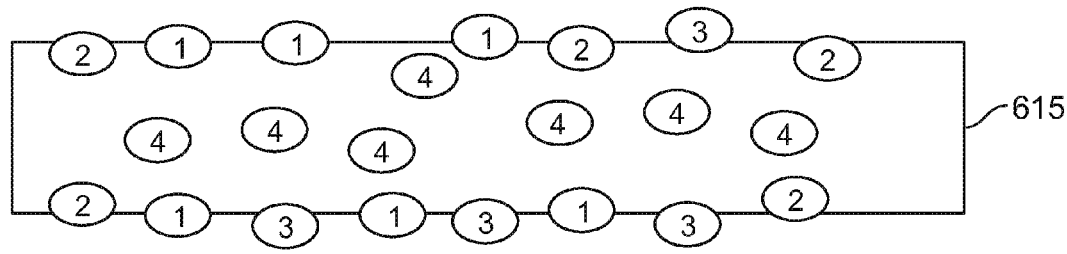
FIG. 10 is an example of a schematic of cells attached on an electrode surface.

FIG. 10 depicts an example of cells 150 totally or partially attached to the surface of a branch element 415. In FIG. 7, cells 150, depicted by 1, are positioned on the edge of the branch element 415 such that half the surface of the cell is attached to the branch element 415, while half of the surface of the cell is not. Cells 150, depicted by 2, are positioned on the edge of the branch element 415 such that more than half of the surface of the cell is attached to the edge of the branch element 415 while the remainder of the surface of the cell is not. Cells 150, depicted by 3, are positioned on the edge of the branch element 415 such that less than half of the surface of the cell is attached to the edge of the branch element 415, while the remainder of the cell is not. Cells 150, depicted by 4, are positioned on the branch element 415 such that the total surface of the cell is attached to the branch element 415. Cells under category 4 can be positioned anywhere on the branch element 415. In some implementations, only the cells that are attached entirely to the branch element 415 can be used to determine cell covered cell-electrode impedance. In other implementations, the contribution to the measured signals from cells that are partially attached to the branch elements 415 can be included.

Both, the cells attached totally and the cells attached partially, can be defined as effective cells that contribute to the impedance. Numerous cells can occupy positions along the edges of the branch elements 415. A branch element 415 can be represented by a length, L, and a width, W. The individual cells on the branch element 415 surface can fall under one of the categories 1, 2, 3, and 4 depicted in FIG. 7. The average area of any cell occupying a position on the edge of the branch element 415 can be considered as equivalent to half the area of a cell 150. The area of a cell 150, in turn, can be represented as the distance of one radius of a cell tangential to the long edge of the branch element 415 for the total length of the edges of the branch elements 415. An effective branch element 415 width, $W_{eff}$, can be defined by equation (10), to account for effective cells along both of the long edges of the branch element 415.

$$W_{eff} = W + 2r_{cell} \quad (10)$$

In addition, the effect of sharp turns of electrodes on the electric field generated by the AC signal, known as the edge effect, can also be accounted for by using the effective branch element width, $W_{eff}$. The sharp turns on the electrode can increase the strength of the local electric field due to electric charge accumulation at the location of the sharp turn. This can alter the total electric field strength of the electrode. The effect of the altered electric field near the sharp turns can be accounted for by at least assuming the width of the branch element, W, to be an effective width, $W_{eff}$, which is set to be greater than the actual width W of the branch element. The relationship regarding the effective electrode width and the effect of the electric field can be complex when the electric field is a non-uniform field caused by the edge effect where the strength of electric field in the edge is higher than that in the middle of the electrode. Experience and various tests have demonstrated that using a properly selected effective electrode width $W_{eff} > W$ can compensate for the non-uniformity of the electric field distribution from the edge to the center of the electrode during the design process of the impedance sensors described in this application. As a result of using this effective electrode width, $W_{eff}$, the design model based on the uniform field distribution over the electrode can be used to design actual sensors where the field distribution is not uniform due to the edge effect. An effective area of the branch element 415, $A_{eff}$, can be defined and represented by equation (11):

$$A_{eff} = W_{eff} \times L \quad (11)$$

In some implementations, the length of the branch element can also be replaced by an effective branch element length, which includes the radius of the cell near the short edge of the branch element 415.

The cell radius, $r_{cell}$, is an intrinsic parameter of the type of the living cell attached to the cell-electrode impedance sensor. Both, the edge effect and $r_{cell}$, can affect the sensitivity of the sensor. As the width of the branch element 415 decreases, the cells which cover the edge of the branch element 415 can occupy a larger portion of the surface are of the branch element 415. Both, $A_{eff}$ and the edge effect, can be manipulated to improve the sensitivity of the sensor and capturing the impedance from a larger number of cells as the width of the branch element 415 decreases.

The accuracy of equations (7) and (8), in predicting the cell free and cell covered cell-electrode impedance, respectively, can be determined by experimentally measuring cell free and cell covered cell-electrode impedances in a cell-electrode impedance measurement system 100 and comparing the measured values to the design prediction. For example, HeLa cell cultures with a cellular radius of about 9.5 µm were studied. Branch elements of widths, W, 20 µm, 40 µm, and 80 µm were chosen. This resulted in effective widths, $W_{eff}$, of 39 µm (20+2*9.5), 59 µm (40+2*9.5), and 99 µm (80+2*9.5), respectively.

Figure 11:
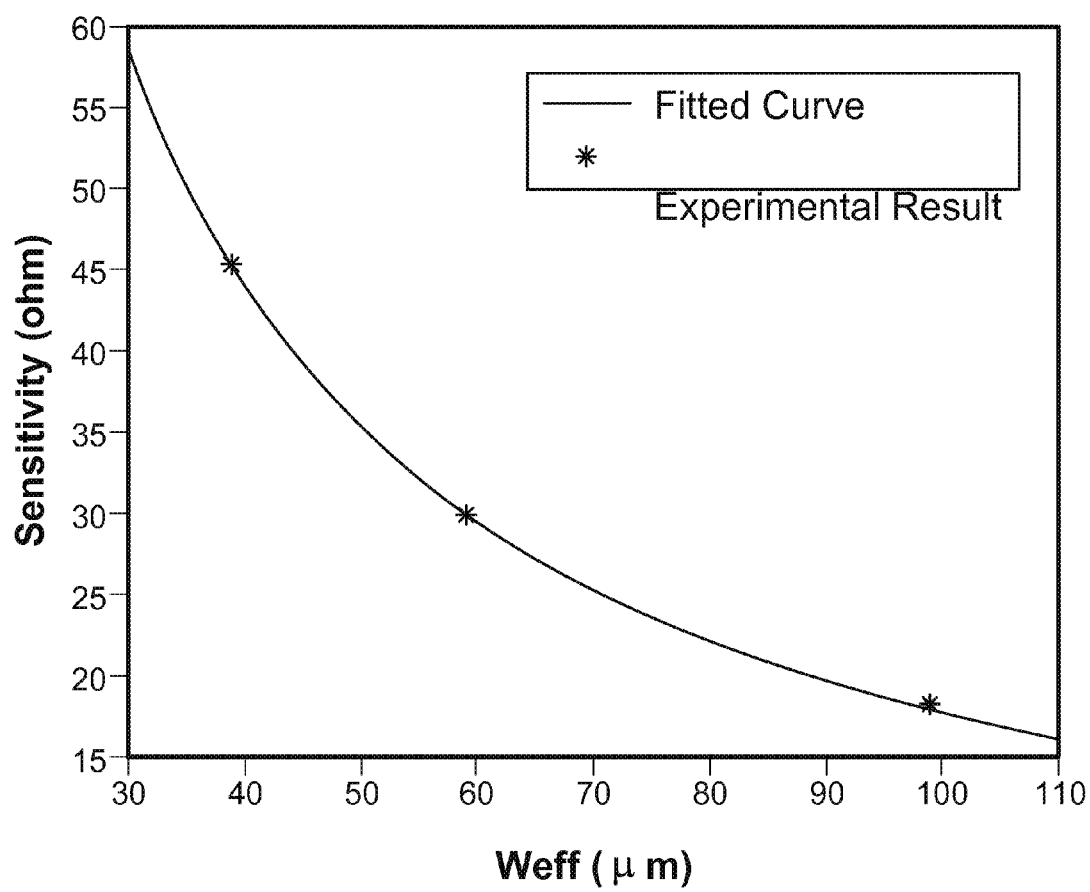
FIG. 11 is a plot validating the design model for cell-electrode impedance.

FIG. 11 depicts a comparison between cell-electrode impedance calculated using equations (7) and (8) and experimentally measured cell-electrode impedance using the HeLa cell cultures. The sensitivity of the cell-electrode impedance measurement system 100 is plotted against the effective widths, $W_{eff}$, of 3 branch elements 415. The experimentally measured sensitivity data, shown in FIG. 11, shows that the measured sensitivity (represented by points in FIG. 11) lies on the computationally obtained fitted curve (represented by the line in FIG. 11).

Figure 12:
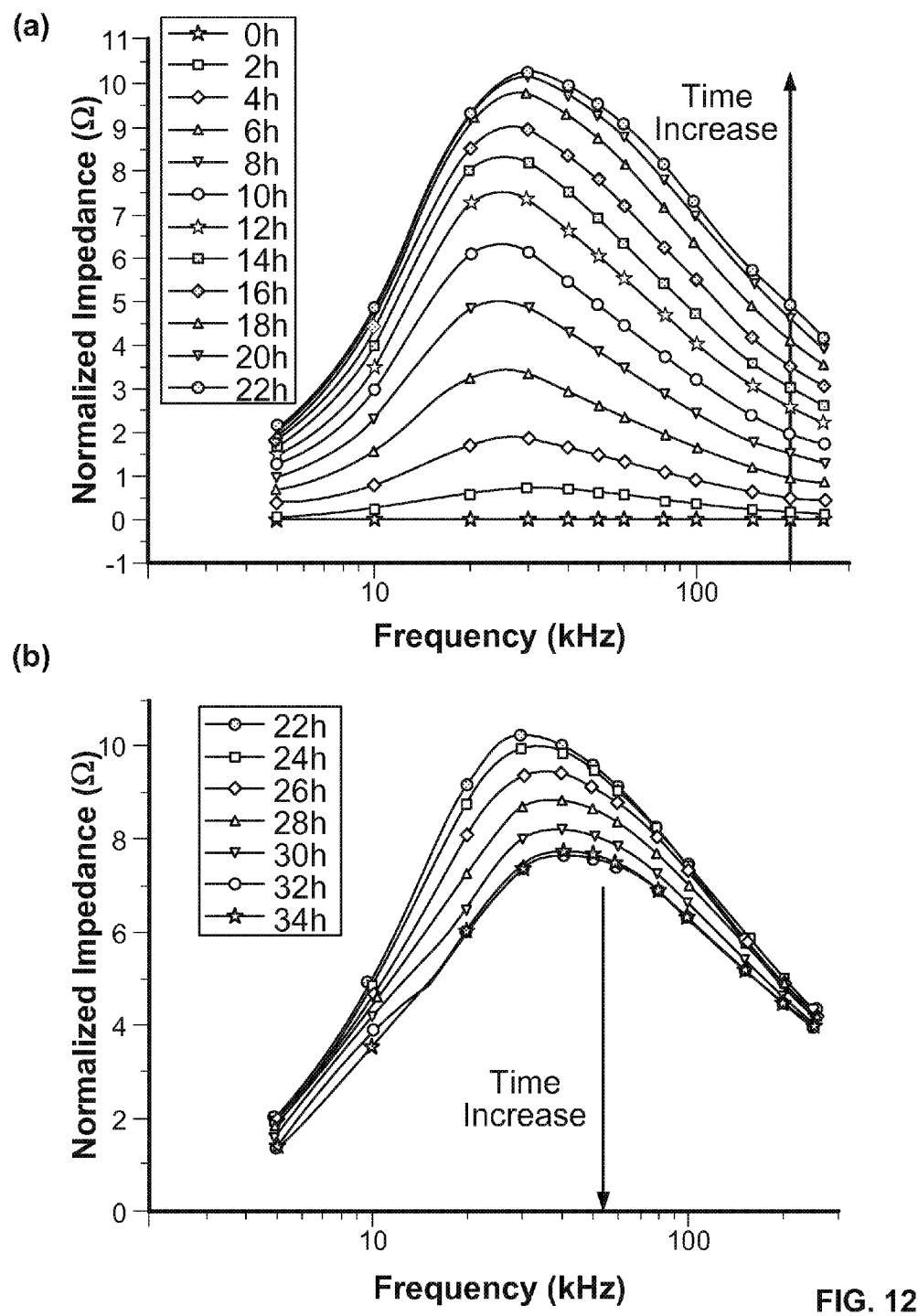
FIG. 12 is a plot of normalized impedance measured over time in response to varied frequency.

FIG. 12 depicts plots of normalized impedance measured over time in response to changing frequency. In the example shown, the cell-electrode impedance was measured during cell proliferation. FIG. 12 shows that during cell proliferation, as time increases, the frequency-dependent normalized impedance increases (FIG. 12, (a)). It can also be seen from FIG. 12 that, during cell proliferation, as time decreases, the frequency-dependent normalized impedance decreases as time increases (FIG. 12, (b)).

Figure 13:
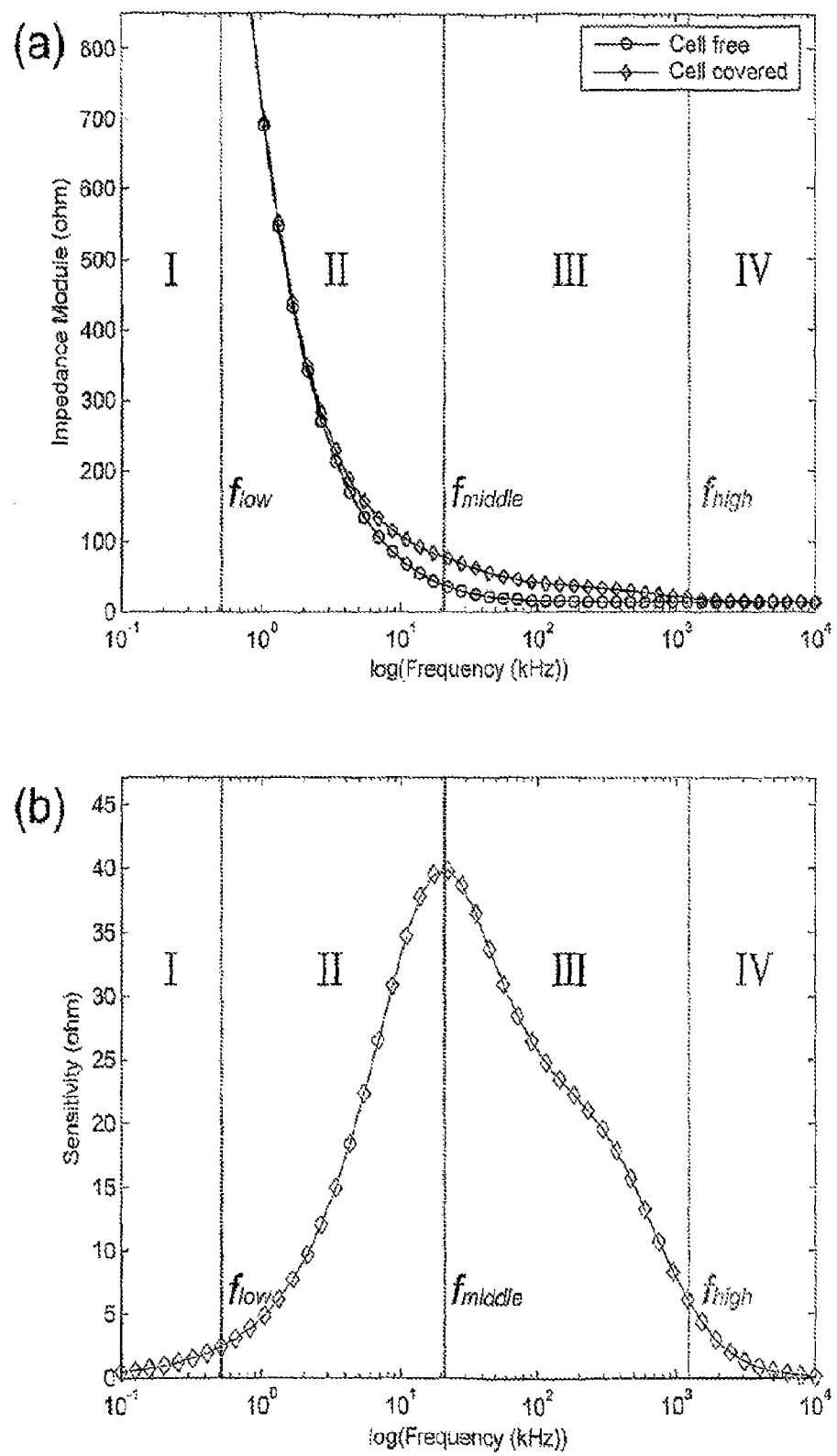
FIG. 13 is a plot of sensor sensitivity in response to changing frequency.

FIG. 13 depicts the frequency characteristics of a cell-electrode impedance sensor. A frequency range to maximize the sensitivity of the cell-electrode impedance measurement system can be determined using the design model. In measuring cell-electrode impedance, AC signals from the AC stimulator 115 can be delivered at different frequencies. Three important frequencies can be deduced from the equivalent circuit proposed in equation (7) and (8), namely, $f_{low}$, $f_{middle}$, and $f_{high}$. In the low frequency range, interface capacitance, $C_I$, dominates resistance and the equivalent impedance circuit can be represented by FIG. 3B. The equivalent circuit which is effective in low frequency range can be a equated to a high-pass circuit and the cut-off frequency at which the impedance of $C_I$ is equal to the sum of $R_S$, $R_{cell}$, and $R_{gap}$ can be defined by equation (12).

$$f_{cut\text{-}off\text{-}low} = \frac{1}{2\pi(R_S + R_{cell} + R_{gap})C_I} \quad (12)$$

A frequency, $f_{low}$, can be defined as lower than one fifth one-fifth of $f_{cut\text{-}off\text{-}low}$. At a frequency lower than $f_{low}$, the impedance of cell covered cell-electrode sensor can be dominated by interface capacitance, $C_I$. In this range, the impedance of cell free cell-electrode sensor is also dominated by $C_I$ and the sensitivity of the sensor can be low. Further, as the frequency decreases, the sensitivity can decrease and approach zero. The frequency, $f_{low}$, can be represented by equation (13).

$$\begin{aligned} f_{low} &= \frac{f_{cut\text{-}off\text{-}low}}{5} \\ &= \frac{1}{10\pi(R_S + R_{cell} + R_{gap})C_I} \\ &= \frac{1}{10\pi\left(\frac{\rho K}{\pi A} + K_1 A^{-1} + K_2 A^{-1}\right)\frac{\varepsilon_0 \varepsilon_\rho A}{d_{dl}}} \\ &= \frac{1}{10\pi\left(\left(\frac{\rho K}{\pi} + K_1 + K_2\right)\frac{\varepsilon_0 \varepsilon_\rho}{d_{dl}}\right)} \end{aligned} \quad (13)$$

In the high frequency range, $R_{cell}$ can dominate $C_{cell}$, and $R_{gap}$ can dominate $C_{gap}$. The equivalent impedance circuit can be represented by FIG. 3C. The equivalent circuit can be equated to a high-pass circuit and the cut off frequency can be represented by equation (14).

$$f_{cut\text{-}off\text{-}high} = \frac{1}{2\pi R_S(C_I^{-1} + C_{cell}^{-1} + C_{gap}^{-1})} \quad (14)$$

A frequency, $f_{high}$, can be defined as five times $f_{cut\text{-}off\text{-}high}$. At a frequency higher than $f_{cut\text{-}off\text{-}high}$, the impedance of both cell free and cell covered cell-electrode impedance can be dominated by $R_S$. Further, the sensitivity can be low and can approach zero as the frequency increases. The frequency, $f_{high}$, can be represented by equation (15).

$$\begin{aligned} f_{high} &= 5 \times f_{cut\text{-}off\text{-}high} \\ &= \frac{5}{2\pi R_S(C_I^{-1} + C_{cell}^{-1} + C_{gap}^{-1})} \\ &= \frac{5}{2\pi \frac{\rho K}{\pi A}\left(\frac{d_{dl}}{\varepsilon_0 \varepsilon_\rho A} + \frac{1}{K_3 A} + \frac{1}{K_4 A}\right)^{-1}} \\ &= \frac{1}{2\pi \frac{\rho K}{\pi}\left(\frac{d_{dl}}{\varepsilon_0 \varepsilon_\rho} + \frac{1}{K_3} + \frac{1}{K_4}\right)^{-1}} \end{aligned} \quad (15)$$

A third frequency, $f_{middle}$, can be defined as the frequency at which the sensitivity can be maximum. This frequency can be determined by solving the derivative of the equation for sensitivity (1). The derivative can be represented by equation (16).

$$\begin{aligned} \frac{d(\text{Sensitivity}(f))}{df} &= \frac{d(|Z_{cell\text{-}covered\text{-}total}(f)| - |Z_{cell\text{-}free\text{-}total}(f)|)}{df} \\ &= 0 \end{aligned} \quad (16)$$

As illustrated in FIG. 13(a), the cell free cell-electrode impedance and the cell covered cell-electrode impedance are nearly equal at frequencies closer to $f_{low}$ and $f_{high}$. The difference between the cell free cell-electrode impedance and the cell covered cell-covered impedance is greatest at frequencies near $f_{middle}$. Since the sensitivity is directly proportional to the difference between the cell covered cell-electrode impedance and the cell free cell-electrode impedance, sensitivity of the impedance measurement system can be maximized at and near a frequency equal to $f_{middle}$. The dimensions of a sensor are independent of the frequency of the AC signal. In some implementations, the sensitivity can be maximized when the frequency range of the input signal is between 10 kHz and 40 kHz. This operating frequency range from 10 kHz to 40 kHz can be determined based on experimental data of the sensors. Equivalent circuit parameters described in this specification can be used to fit to measured experimental data to determine equivalent circuit parameters and the resultant equivalent circuit parameters are then applied to the circuit equations to calculate the operating frequency range for the sensor.

Figure 14:
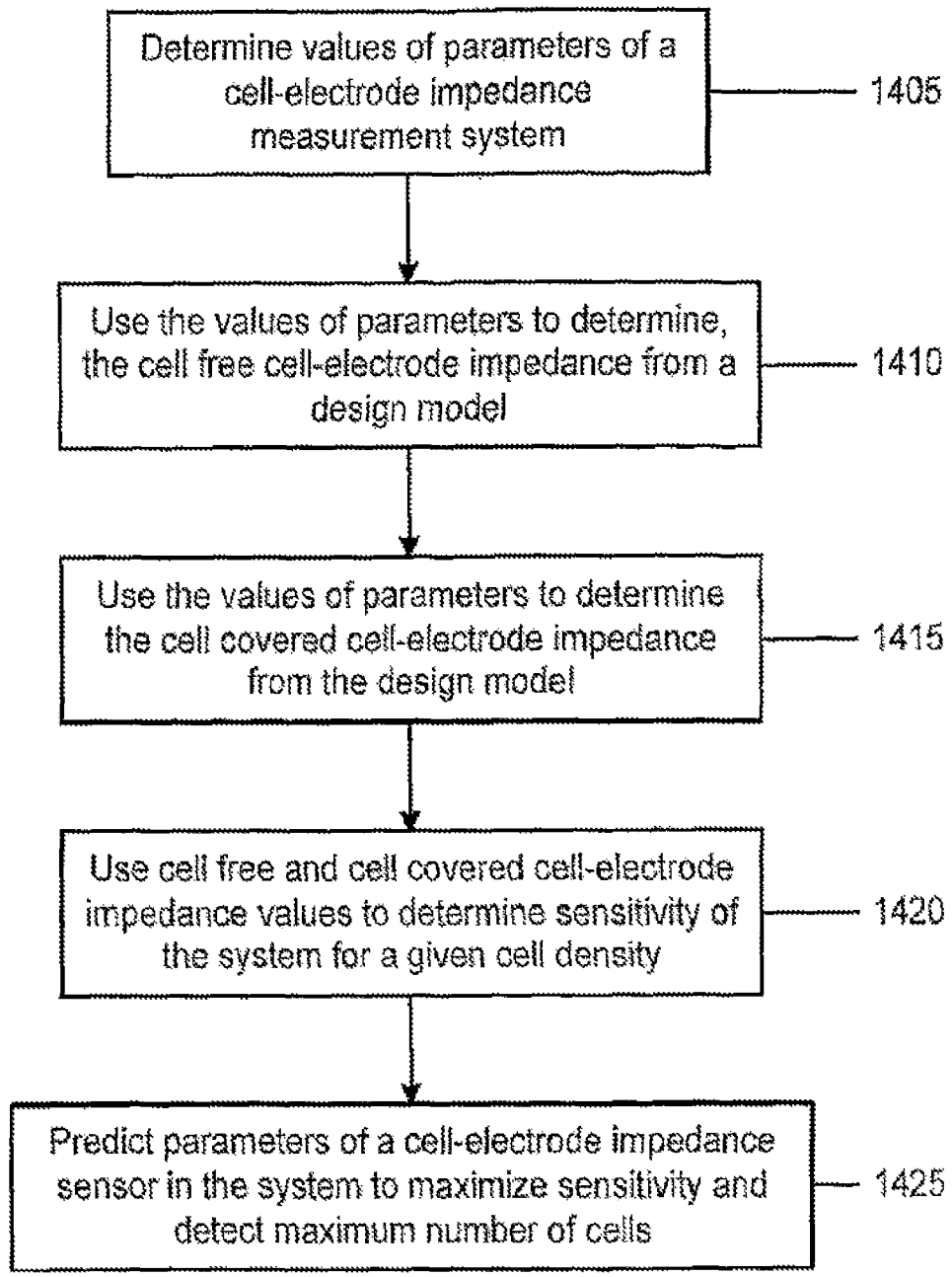
FIG. 14 is a flow chart of an example of designing a cell-electrode impedance measurement system.

FIG. 14 depicts a flow chart of an example of designing a cell-electrode impedance measurement system. The values of parameters of the system can be determined at 1405. The parameters can include one or more of the properties of the cell culture vessel, the culture medium, the culture cells, the proportion coefficients to represent $R_{gap}$, $R_{cell}$, $C_{gap}$, and $C_{cell}$, etc. The cell free cell-electrode impedance can be determined from a design model at 1410. The cell free cell-electrode impedance can be determined using equation (7). The cell covered cell-electrode impedance can be determined from the design model at 1415. The computational cell covered cell-electrode impedance can be determined using equation (8). Using the computationally determined cell free and cell covered cell-electrode impedances, the sensitivity of a system can also be determined at 1420. The computational sensitivity can be determined using equation (1). The computational cell free and cell covered cell-electrode impedances can be used to predict parameters of a cell-electrode impedance sensor in the system at 1425. The cell-electrode impedance sensor can be an interdigitated array. The predicted parameters can include the area of the branch elements of the interdigitated array, the width of the branch elements, and the number of branch elements. Based on equations (7) and (8), the sensitivity of the sensor is inversely proportional to the area of the branch elements and the number of branch elements. In addition, the area of the branch elements and the number of elements is directly proportional to the number of cells that can be studied. By predicting the cell-electrode impedances, a sensor can be designed that can maximize sensitivity while also maximizing the number of cells that can be studied.

Figure 15:
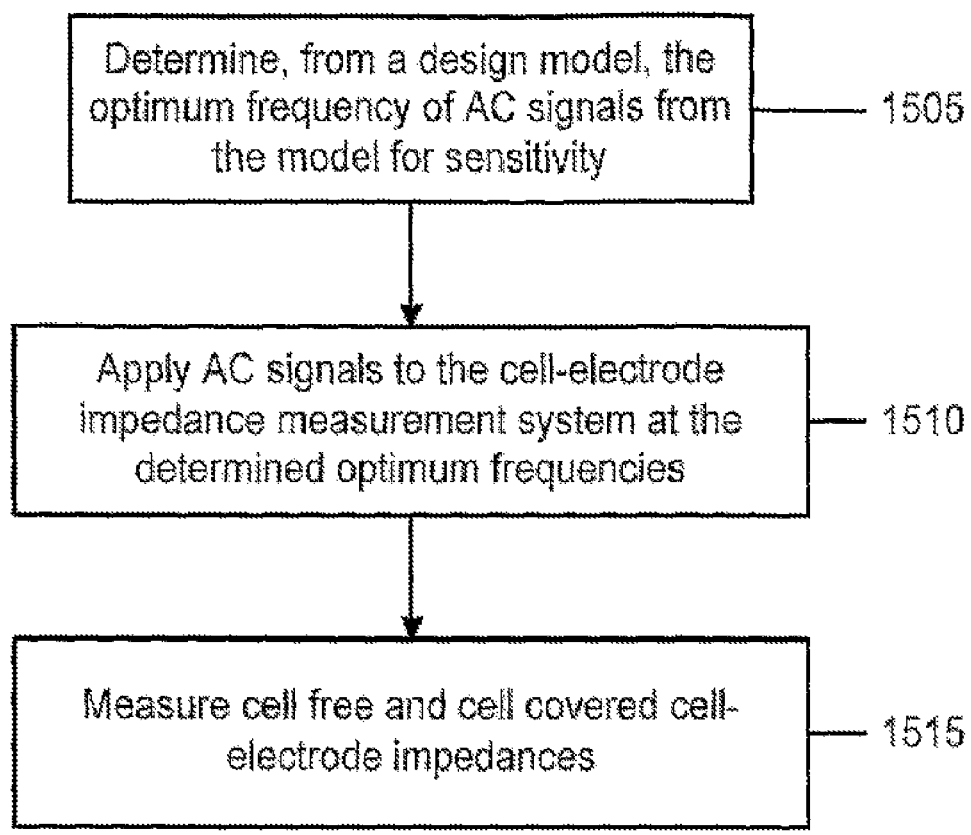
FIG. 15 is a flow chart of an example of maximizing sensitivity of a cell-electrode impedance measurement system.

FIG. 15 depicts a flow chart of an example of optimizing the frequency of AC signals applied to a cell-electrode impedance measurement system. Based on the sensitivity of the cell-electrode impedance measurement system, determined from equation (1), and the cell free and cell covered cell-electrode impedances determined from equations (7) and (8), the optimum frequency of AC signals can be determined at 1505. In some implementations, the equations representing cell free cell-electrode impedance (7) and cell covered cell-electrode impedance (8) can be substituted into the equation representing sensitivity equation (1). The equation representing sensitivity can be differentiated with respect to frequency and the resulting expression can be set to zero. A solution to the equation can yield an optimum frequency value. AC signals can be applied to the cell-electrode impedance measurement system at the determined optimum frequencies at 1510. The cell free and cell covered cell-electrode impedances of the system can be measured at 1515.

Hence, one design model for designing a cell-electrode impedance sensor system is based on an equivalent circuit model for interdigitated array structure cell-electrode impedance sensor, including a first equivalent circuit model the cell free sensor and a second equivalent circuit model for the cell covered sensor. The equivalent circuit model in this design model can include parameters Rcell, Ccell, Rgap and Cgap. Rcell is the resistance of the mean gap distance between the cells which are attached on the electrodes of the sensor. This parameter can be used to monitor the mean gap distance between cells in real time. Ccell is the capacitance of cells created by their insulating cell membranes. This parameter can reflect changes in the biophysical properties of the cell membranes. Rgap is the resistance of the gap between the attached cells and the electrode surfaces. This parameter can be used in real time monitor the mean gap between the attached cells and electrode surface substrate. Cgap is the capacitance between the attached cells and the electrode surface substrate. This parameter can be used to reflect the gap between attached cell membranes and electrode surface substrate.

Part or entirety of the design processes described in this specification may be implemented as computer-implemented processes. The design parameters obtained from the described design processes can be used to fabricate sensor devices in a wide range of applications including sensing biological cells.

While this specification contains many specifics, these should not be construed as limitations on the scope of any invention or of what may be claimed, but rather as descriptions of features specific to particular embodiments. Certain features that are described in this specification in the context of separate embodiments can also be implemented in combination in a single embodiment. Conversely, various features that are described in the context of a single embodiment can also be implemented in multiple embodiments separately or in any suitable subcombination. Moreover, although features may be described above as acting in certain combinations and even initially claimed as such, one or more features from a claimed combination can in some cases be excised from the combination, and the claimed combination may be directed to a subcombination or variation of a subcombination. Only a few implementations and examples are described. However, other variations, modifications, and enhancements are possible and are within the scope of the following claims.

What is claimed is:

1. An apparatus for measuring cell-electrode impedance in biological cells, comprising:
   a cell-culture vessel comprising electrodes structured in an interdigitated array of electrode branch elements, the cell-culture vessel operable to hold a cell-culture medium having biological cells attachable to the electrodes and the electrode branch elements arranged to be staggered with a non-uniform distance between each of the electrode branch elements; and
   circuitry electrically coupled to the electrodes and comprising a detection resistor and a stimulator to apply an alternating current (AC) signal at different frequencies to the electrodes and configured to control a frequency range of the AC signal to be between a low frequency and a high frequency; wherein
   the electrodes have an equivalent electrical circuit that is dominated by interface capacitance at the low frequency and is dominated by spreading resistance at the high frequency.

2. The apparatus of claim 1, wherein the electrodes are located in the cell-culture vessel at a location to be immersed in the cell culture medium in the cell-culture vessel when the cell culture medium is present.

3. The apparatus of claim 1, wherein the electrode branch elements include first electrode branch elements connected to a first electrical terminal of the circuitry and second electrode branch elements connected to a second electrical terminal of the circuitry, wherein the first and second electrode branch elements are interleaved and the circuitry applies the AC signal at the first and second electrical terminals.

4. The apparatus of claim 1, wherein each branch element has a width from 10 µm to 100 µm.

5. The apparatus of claim 1, wherein the cell-culture vessel comprises a bio-compatible insulating material.

6. The apparatus of claim 5, further comprising a vessel substrate that is manufactured from a same material as the cell-culture vessel.

7. The apparatus of claim 1, further including:
   a digital signal processor that collects and stores values of at least one of the AC signal and a voltage difference between electrodes.

8. The apparatus of claim 1, wherein the interdigitated array of electrode branch elements includes a first electrode comprising interleaved branch elements and a second electrode comprising second interleaved branch elements.

9. The apparatus of claim 1, wherein the sensitivity of the electrodes corresponds to smallest impedance caused by presence of cells in the cell-culture vessel that can be measured by the apparatus.

10. The apparatus of claim 1, wherein the sensitivity is a function of a cell-free impedance of the electrodes, a cell-covered impedance of the electrodes and a density of the biological cells.

11. The apparatus of claim 1, wherein the sensitivity of the electrodes is a function of frequency of the AC signal.

12. A cell-electrode impedance sensor for use in a cell-electrode impedance measurement system, comprising:
   an interdigitated electrode array comprising a plurality of branch elements that have non-uniform actual widths and are separated by non-uniform distances, the plurality of branch elements characterized by design parameters including one or more effective widths of the branch elements, a length of the branch elements, a surface area of the branch elements, and a number of the branch elements; wherein the design parameters are determined based on a design model for the cell-electrode impedance sensor, the design model predicting a cell free cell-electrode impedance and a cell covered cell-electrode impedance; and wherein each of the non-uniform actual widths of the branch elements is less than each of the effective width of the branch elements obtained based on the design parameters, to account for a non-uniform electric field distribution over each branch element;

wherein the interdigitated electrode array has an equivalent electrical circuit that is dominated by interface capacitance at a low frequency and is dominated by spreading resistance at a high frequency.

13. The cell-electrode impedance sensor of claim 12, wherein the cell-electrode impedance measurement system includes one or more of a cell culture vessel, a cell culture substrate, and circuitry.

14. The cell-electrode impedance sensor of claim 12, wherein the cell-electrode impedance sensor is fabricated using various materials such as glass, silicon and plastics.

15. The cell-electrode impedance sensor of claim 12, wherein the cell-electrode impedance measurement system includes:
a digital signal processor that collects and stores values of at least one a current signal and a voltage difference signal of the cell-electrode impedance sensor.

16. The cell-electrode impedance sensor of claim 12, wherein the interdigitated electrode array includes a first electrode comprising interleaved branch elements and a second electrode comprising second interleaved branch elements.

17. The cell-electrode impedance sensor of claim 12, wherein the sensor sensitivity corresponds to smallest impedance caused by presence of cells in the cell-culture vessel that can be measured by the apparatus.

* * * * *